(12) United States Patent
Hwang (10) Patent No.: US 9,421,319 B2
(45) Date of Patent: Aug. 23, 2016

(54) BLOOD SEPARATION CONTAINER FOR EXTRACTING SELF-PLATELET

(71) Applicant: Good morning Bio Co., Ltd., Incheon (KR)

(72) Inventor: Eui Jae Hwang, Incheon (KR)

(73) Assignee: Good morning Bio Co., Ltd., Incheon (KR)

( * ) Notice: Subject to any disclaimer, the term of this patent is extended or adjusted under 35 U.S.C. 154(b) by 0 days.

(21) Appl. No.: 14/878,988

(22) Filed: Oct. 8, 2015

(65) Prior Publication Data

US 2016/0030661 A1  Feb. 4, 2016

Related U.S. Application Data

(63) Continuation of application No. PCT/KR2014/003073, filed on Apr. 9, 2014.

(30) Foreign Application Priority Data

Apr. 11, 2013 (KR) .................. 10-2013-0039895
Aug. 21, 2013 (KR) .................. 20-2013-0007002 U
Oct. 28, 2013 (KR) .................. 20-2013-0008820 U (51) Int. Cl.
*A61M 1/36* (2006.01)
*A61M 1/02* (2006.01)
(Continued)

(52) U.S. Cl.
CPC ........... *A61M 1/3696* (2014.02); *A61M 1/0259* (2013.01); *A61M 1/0272* (2013.01); *A61M 1/3693* (2013.01); *B01L 3/5021* (2013.01); *G01N 1/4077* (2013.01); *G01N 33/49* (2013.01);
(Continued)

(58) Field of Classification Search
CPC ............ A61M 1/3696; A61M 1/3693; A61M 1/0259; A61M 1/0272; G01N 33/49; G01N 1/4077; B01L 3/5021; B01L 2400/0478
See application file for complete search history.

(56) References Cited

U.S. PATENT DOCUMENTS 6,506,167 B1  1/2003  Ishimito et al.
6,905,612 B2  6/2005  Dorian et al.
(Continued)

FOREIGN PATENT DOCUMENTS

CN    101765437 A   6/2010
JP    2004-536794 A  12/2004
(Continued)

OTHER PUBLICATIONS

Translation of the Chapter I International Preliminary Report on Patentability for PCT/KR2014/003073, dated Oct. 13, 2015.*

(Continued)

*Primary Examiner* — David A Reifsnyder
(74) *Attorney, Agent, or Firm* — IP Legal Services, LLC (57) ABSTRACT

The present invention relates to a blood separation container for extracting self-platelet.

According to the present invention, since a second coupling portion is formed at a release prevention member coupled to a lower portion of a main body in a PRP separation container, and an ascending member having a bolt structure is screwed to the second coupling portion to ascend a lower cover disposed in a lower fluid chamber of the main body, a separate second main body is unnecessary unlike the related art. Therefore, the PRP separation container is easy to carry, manufacturing costs can be reduced to thereby ensure competitive price, and a PRP can be easily separated and extracted.

7 Claims, 6 Drawing Sheets

(51) Int. Cl.
 *G01N 33/49* (2006.01)
 *G01N 1/40* (2006.01)
 *B01L 3/00* (2006.01)

(52) U.S. Cl.
 CPC ........ *B01L 2200/16* (2013.01); *B01L 2300/044* (2013.01); *B01L 2300/0858* (2013.01); *B01L 2400/0478* (2013.01); *G01N 2001/4083* (2013.01)

(56) References Cited

U.S. PATENT DOCUMENTS

| | | |
|---|---|---|
| 7,223,346 B2 | 5/2007 | Dorian et al. |
| 7,470,371 B2 | 12/2008 | Dorian et al. |
| 7,806,276 B2 | 10/2010 | Leach et al. |
| 7,837,884 B2 | 11/2010 | Dorian et al. |
| 8,187,477 B2 | 5/2012 | Dorian et al. |
| 2002/0182664 A1 | 12/2002 | Dolecek et al. |
| 2003/0233064 A1 | 12/2003 | Arm et al. |
| 2004/0182795 A1 | 9/2004 | Dorian et al. |
| 2005/0186120 A1 | 8/2005 | Dorian et al. |
| 2006/0151384 A1 | 7/2006 | Ellsworth et al. |
| 2010/0211041 A1 | 8/2010 | Omori et al. |
| 2011/0003276 A1 | 1/2011 | Arm et al. |
| 2013/0011311 A1 | 1/2013 | Kim |
| 2013/0189668 A1 | 7/2013 | Arm et al. |
| 2014/0205514 A1 | 7/2014 | Hwang |
| 2015/0144561 A1 | 5/2015 | Arm et al. |

FOREIGN PATENT DOCUMENTS

| | | |
|---|---|---|
| JP | 2005-523128 A | 8/2005 |
| JP | 2005-524451 A | 8/2005 |
| KR | 10-2010-0105282 A | 9/2010 |
| KR | 10-2011-0009651 A | 1/2011 |
| KR | 10-1026599 B1 | 4/2011 |
| KR | 10-1128163 B1 | 3/2012 |
| KR | 10-1279652 B1 | 7/2013 |

OTHER PUBLICATIONS

Korean Intellectual Property Office, International Search Report for International Application No. PCT/KR2012/005675, Jan. 28, 2013.
Korean Intellectual Property Office, International Search Report for International Application No. PCT/KR2014/003073, Jul. 30, 2014.

* cited by examiner

BLOOD SEPARATION CONTAINER FOR EXTRACTING SELF-PLATELET

CROSS REFERENCE TO PRIOR APPLICATIONS

This application is a continuation application under 35 U.S.C. §365(c) of International Application No. PCT/KR2014/003073 (filed on Apr. 9, 2014) designating the United States, which claims priority to Korean Patent Application Nos. 10-2013-0039895 (filed on Apr. 11, 2013), 20-2013-0007002 (filed on Aug. 21, 2013) and 20-2013-0008820 (filed on Oct. 28, 2013), which are all hereby incorporated by reference in their entireties.

TECHNICAL FIELD

The present invention relates to a blood separation container for extracting self-platelet.

BACKGROUND ART

Generally, blood is used as an important index for determining various diseases or health conditions. Platelets abundantly containing growth factors in the blood are used for therapeutic purposes. Blood is composed of red blood cells, white blood cells, and platelets, and the platelets mainly exist in a plasma. The plasma is divided into a platelet rich plasma (PRP) and a platelet poor plasma (PPP). The PRP is transplanted into a pain area, in particular, knees, ligaments, muscles, or the like, and stimulates stem cells to help in creating cells. As such, the PRP has been used for therapeutic purposes.

Since the PRP is a small amount of about 1% in a collected blood and its viscosity is high, it is difficult to separate the PRP from red blood cells. Therefore, research has been actively conducted on technologies for extracting a PRP other than red blood cells. Generally, after blood collected from a human body is injected into a PRP separation container, the PRP is extracted using a centrifuge. In the past, a test tube has been commonly used as the PRP separation container. However, since the PRP extraction is inconvenient, a separation container with a fluid chamber divided into two chambers has recently been developed and used.

An example of the PRP separation container has been proposed in Korean Patent Registration No. 10-1128163 (registration date: Mar. 12, 2012) by the inventor of the present application and is illustrated in FIG. 1.

Figure 1:
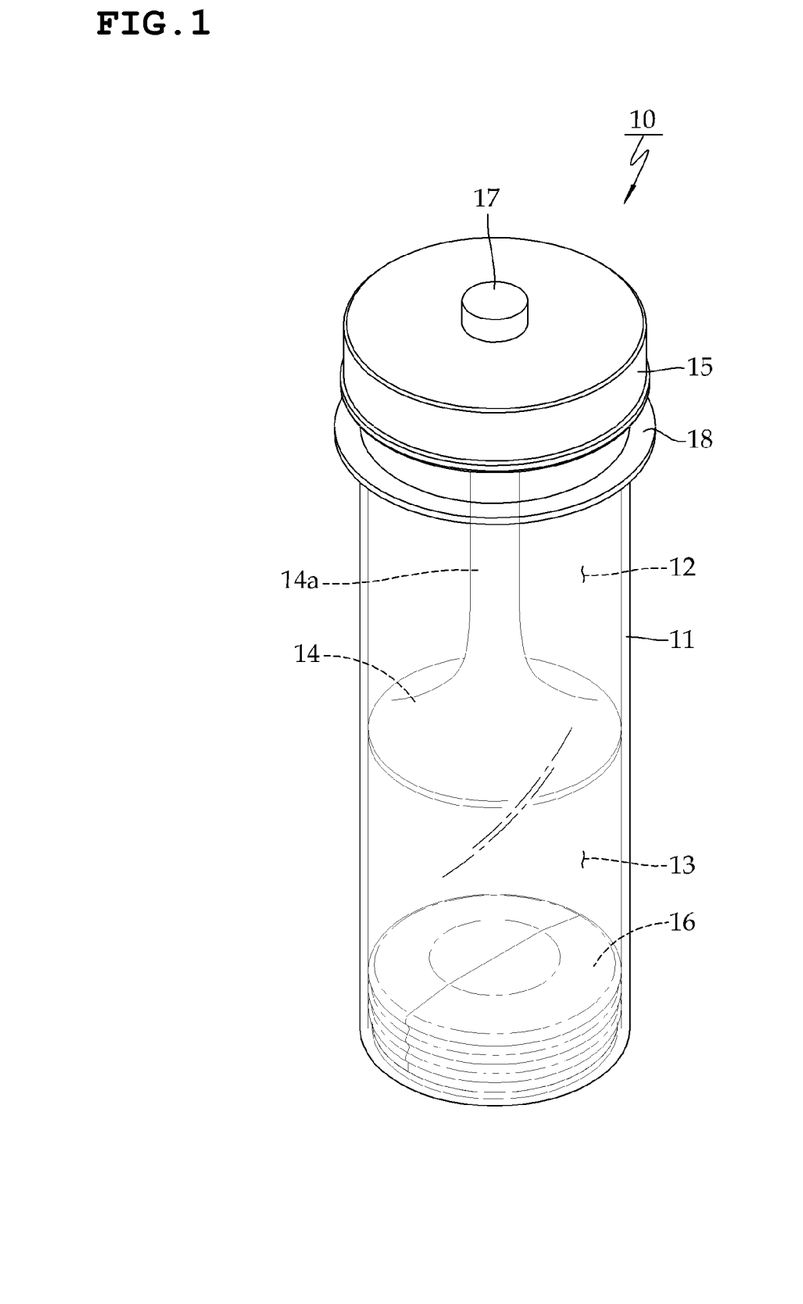
FIG. 1 is a perspective view of a PRP separation container according to the related art.

FIG. 1 is a perspective view for describing a PRP separation container according to the related art.

As illustrated in FIG. 1, the PRP separation container 10 according to the related art includes: a main body 11 defining an internal space divided into an upper fluid chamber 12 and a lower fluid chamber 13; an upper cover 15 disposed to seal an upper portion of the upper fluid chamber 12; a lower cover 16 disposed to seal a lower portion of the lower fluid chamber 13 and coupled to be ascendable in such a state that an outer peripheral surface of the lower cover 16 comes into close contact with an inner peripheral surface of the lower fluid chamber 13 by an external force applied upward; and a fluid collection part 14 dividing the internal space into the upper fluid chamber 12 and the lower fluid chamber 13 and including a fluid passage protruding upward from a central portion to communicate the upper fluid chamber 12 with the lower fluid chamber 13.

A PRP extracting method using the PRP separation container 10 will be described below.

First, blood collected from a human body is injected into the lower fluid chamber 13 by using a syringe, and a centrifugation is performed on the PRP separation container 10, into which the blood is injected, by using a centrifuge.

When the centrifugation is completed, the blood is separated into a red blood cell, a PRP, and a PPP in this order from the lower portion of the lower fluid chamber 13 due to a specific gravity difference. Next, the PPP partially accommodated in the lower fluid chamber 13 is introduced into the upper fluid chamber 12 through a fluid passage 14a by ascending the lower cover 16.

After that, plasma accommodated in the lower fluid chamber 13 is introduced into the upper fluid chamber 12 through the fluid passage 14a by continuously ascending the lower cover 16. In a state in which the PRP exists in the fluid passage 14a, a syringe is inserted into the fluid passage 14a through an injection port of the upper cover 15, and the PRP existing in the fluid passage 14a is extracted. In this way, the PRP can be easily separated and extracted.

However, in order to ascend the lower cover disposed inside the PRP separation container, the PRP separation container according to the related art, which is proposed in Korean Patent Registration No. 10-1128163, has necessarily need the main body having a relatively complex structure. Accordingly, since it is necessary to separately manufacture the main body, a manufacturing cost of the main body increases and thus a manufacturing cost of the PRP separation container increases. This undermines price competitiveness and the PRP separation container is difficult to carry.

On the other hand, recently, fibrin has been extracted by separating PRP and PPP using the above-described PRP separation container and then solidifying the separated PRP and PPP. The fibrin has been used as a base of an implant for a dental treatment, and the demand for the fibrin has been steadily increased. If the demand for the fibrin extends to an orthopedic area, the demand for the fibrin is expected to explosively increase.

When the PRP and the PPP are exposed to air, the PRP and the PPP begin to naturally coagulate. However, since a long time is taken until the PRP and the PPP coagulate, a reduction in a coagulation time is most important in terms of productivity. Therefore, in a state in which the PRP and PPP remains in the upper fluid chamber of the PRP separation container, in which the PRP and the PPP are separated from each other, the PRP and the PPP are coagulated by using the centrifuge again. In this manner, the coagulation time of the PRP and the PPP has been reduced to some extent.

Although the method of coagulating the PRP and the PPP using the centrifuge as in the related art can reduce the coagulation time of the PRP and PPP to some extent, about 20 minutes to about 30 minutes are taken until the PRP and the PPP coagulate, resulting in a reduction in productivity. Therefore, there is a need for research and development of technologies capable of reducing the coagulation time.

CITATION LIST

Patent Literature

KR 10-1026599 B1, 2011. Mar. 25. pp. 3-6
KR 10-2011-0009651 A, 2011. Jan. 28. pp. 3-7
KR 10-1128163 B1, 2012. Mar. 12. pp. 6-8, FIGS. 1 to 5

SUMMARY OF INVENTION

Technical Problem

Therefore, the present invention has been made in an effort to solve the problems of the related art and have the following objects.

First, an object of the present invention is to provide a blood separation container for extracting self-platelet, which is capable of easily separating and extracting a PRP while reducing manufacturing costs to thereby ensure competitive price.

Second, another object of the present invention is to provide a blood separation container for extracting self-platelet, which is capable of rapidly coagulating a PRP and a PPP separated from blood to thereby improve extraction productivity of fibrin.

Third, another object of the present invention is to provide a blood separation container for extracting self-platelet, which is capable of improving a collect rate of a buffy coat.

Solution to Problem

According to an aspect for achieving the above objects, a blood separation container includes: a main body defining an inner space divided into an upper fluid chamber and a lower fluid chamber; an upper cover sealing the upper fluid chamber; a lower cover ascending along an inner peripheral surface of the lower fluid chamber in such a state that an outer peripheral surface of the lower cover comes into close contact with the inner peripheral surface of the lower fluid chamber; a fluid collection part which is formed between the upper fluid chamber and the lower fluid chamber and includes a fluid passage protruding upward from a central portion to communicate the upper fluid chamber and the lower fluid chamber; a release prevention member which is coupled to an outer peripheral surface of the main body and includes a first coupling portion and a second coupling portion that communicates with the first coupling portion, a thread being formed on an inner peripheral surface of the first coupling portion so as to be coupled to a thread formed on a lower outer peripheral surface of the main body, and a thread being formed on an inner peripheral surface of the second coupling portion so as to have a diameter less than a diameter of the first coupling portion; and an ascending member which is inserted into and coupled to the second coupling portion of the release prevention member, a portion of which is screwed to the second coupling portion of the release prevention member in a bolt structure, and which is carried in the lower fluid chamber of the main body and varies in a variation in a volume of the lower fluid chamber by ascending the lower cover coming into close contact with the inner peripheral surface of the lower fluid chamber.

According to another aspect for achieving the above objects, a blood separation container includes: a body defining an inner space divided into an upper fluid chamber and a lower fluid chamber; an upper cover sealing the upper fluid chamber; a lower cover ascending along an inner peripheral surface of the lower fluid chamber in such a state that an outer peripheral surface of the lower cover comes into close contact with the inner peripheral surface of the lower fluid chamber; and a fluid collection part which is formed in a funnel shape and includes a fluid passage communicating the lower fluid chamber and the upper fluid chamber, the funnel shape having a mountain-shaped structure that extends from an inner sidewall of the main body to a central portion of the main body at a boundary between the upper fluid chamber and the lower fluid chamber and protrudes toward the upper fluid chamber from the inner sidewall to the central portion, wherein the fluid passage is formed such that an angle of an inlet side in the fluid passage, which is opposed to the lower fluid chamber, is in the range of 70° to 85°.

Preferably, the blood separation container may further include a release prevention member coupled to a lower outer peripheral surface of the main body, and the release prevention member may include a first coupling portion and a second coupling portion that communicates with the first coupling portion, a thread being formed on an inner peripheral surface of the first coupling portion so as to be coupled to a thread formed on a lower outer peripheral surface of the main body, and a thread being formed on an inner peripheral surface of the second coupling portion so as to have a diameter less than a diameter of the first coupling portion.

Preferably, the blood separation container may further include an ascending member inserted into and coupled to the second coupling portion, and a portion of the ascending member may be screwed to the second coupling portion of the release prevention member in a bolt structure, and the ascending member may be carried in the lower fluid chamber of the main body and vary in a variation in a volume of the lower fluid chamber by ascending the lower cover coming into close contact with the inner peripheral surface of the lower fluid chamber.

In addition, according to another aspect for achieving the above objects, a blood separation container includes: a body defining an inner space divided into an upper fluid chamber and a lower fluid chamber; an upper cover sealing the upper fluid chamber; a lower cover ascending along an inner peripheral surface of the lower fluid chamber in such a state that an outer peripheral surface of the lower cover comes into close contact with the inner peripheral surface of the lower fluid chamber; a fluid collection part which is formed between the upper fluid chamber and the lower fluid chamber and includes a fluid passage protruding upward from a central portion to communicate the upper fluid chamber and the lower fluid chamber; and a coagulation catalyst body made of a circular tube including a glass material and inserted into the upper fluid chamber or the lower fluid chamber to function as a catalyst such that a platelet rich plasma (PRP) and a platelet poor plasma (PPP) rapidly coagulate at the time of coagulating the PRP and the PPP by using a centrifuge.

Preferably, the blood separation container may further include a release prevention member coupled to a lower outer peripheral surface of the main body, and the release prevention member may include a first coupling portion and a second coupling portion that communicates with the first coupling portion, a thread being formed on an inner peripheral surface of the first coupling portion so as to be coupled to a thread formed on a lower outer peripheral surface of the main body, and a thread being formed on an inner peripheral surface of the second coupling portion so as to have a diameter less than a diameter of the first coupling portion.

Preferably, the blood separation container may further include an ascending member inserted into and coupled to the second coupling portion, and wherein a portion of the ascending member may be screwed to the second coupling portion of the release prevention member in a bolt structure, and the ascending member may be carried in the lower fluid chamber of the main body and vary in a variation in a volume of the lower fluid chamber by ascending the lower cover coming into close contact with the inner peripheral surface of the lower fluid chamber.

Advantageous Effects of Invention

As described above, according to the present invention, the following effects can be obtained.

First, according to the present invention, since a second coupling portion is formed at a release prevention member coupled to a lower portion of a main body in a PRP separation container, and an ascending member having a bolt structure is screwed to the second coupling portion to ascend a lower cover disposed in a lower fluid chamber of the main body, a separate second main body is unnecessary unlike the related art. Therefore, the PRP separation container is easy to carry, manufacturing costs can be reduced to thereby ensure competitive price, and a PRP can be easily separated and extracted.

Second, according to the present invention, since a secondary centrifugation is performed in a state in which a coagulation catalyst body made of a glass material is inserted into an upper fluid chamber or a lower fluid chamber of the PRP separation container, a coagulation time of a PRP and a PPP can be significantly reduced, thereby improving extraction productivity of fibrin.

Third, according to the present invention, by providing the PRP separation container including a buffy coat extraction tube, which extracts a buffy coat generated after a centrifugation and of which an inlet has an angle range of 70° to 80°, a collect rate of the buffy coat can be increased by minimizing a loss of a portion of the buffy coat due to the adhering of the buffy coat to an inner surface of the buffy coat extraction tube during extracting of the buffy coat after the centrifugation.

DESCRIPTION OF REFERENCE NUMERALS

20: blood separation container
21: main body
22: upper fluid chamber
23: lower fluid chamber
24: fluid collection part
24a: fluid passage
25: upper cover
26: lower cover
27: coagulation catalyst body
28: reinforcement member
29: release prevention member
30: packing member
31: fixing pin
32: ascending member

DESCRIPTION OF EMBODIMENTS

Hereinafter, technical features of the present invention will be described in detail with reference to the accompanying drawings.

Figure 2:
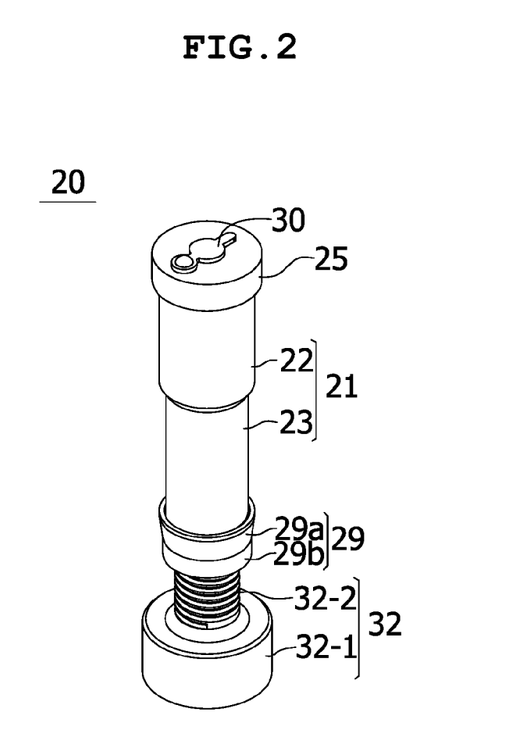
FIG. 2 is an assembly perspective view of a blood separation container according to an embodiment of the present invention.
Figure 3:
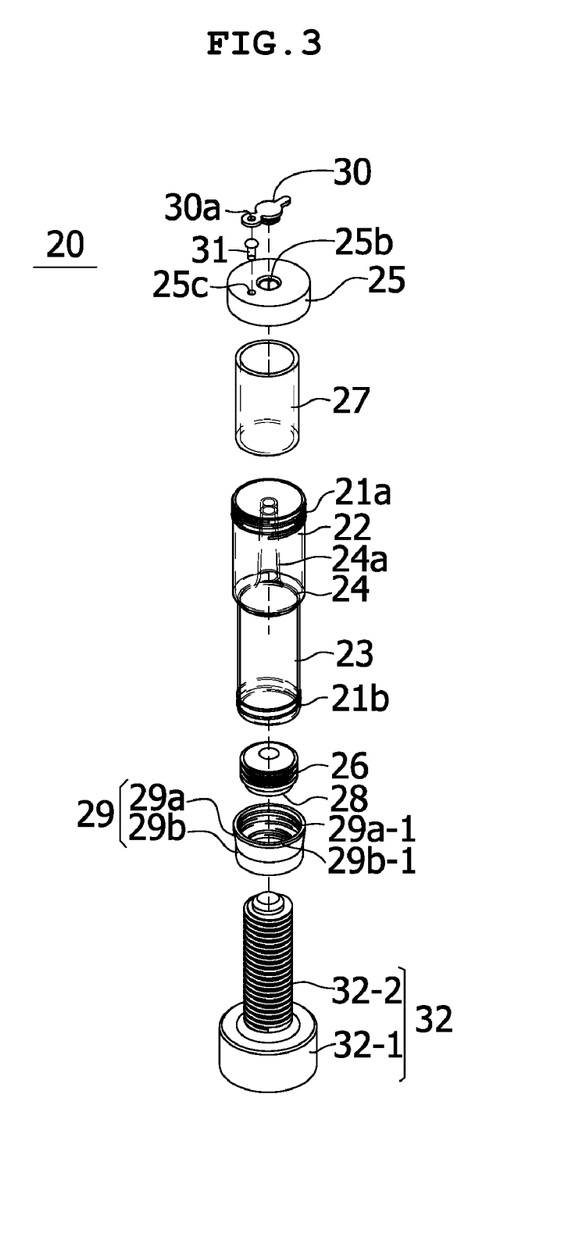
FIG. 3 is an exploded perspective view of the blood separation container illustrated in FIG. 2.
Figure 4:
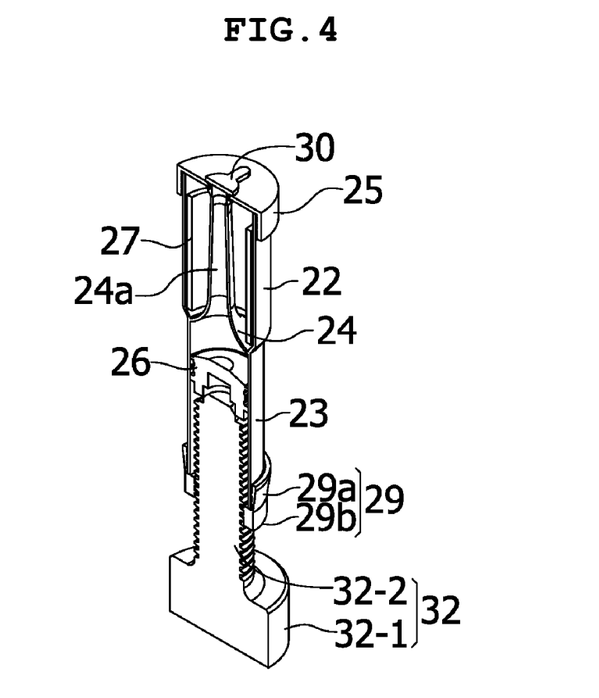
FIG. 4 is a cross-sectional perspective view of the blood separation container illustrated in FIG. 2.
Figure 5:
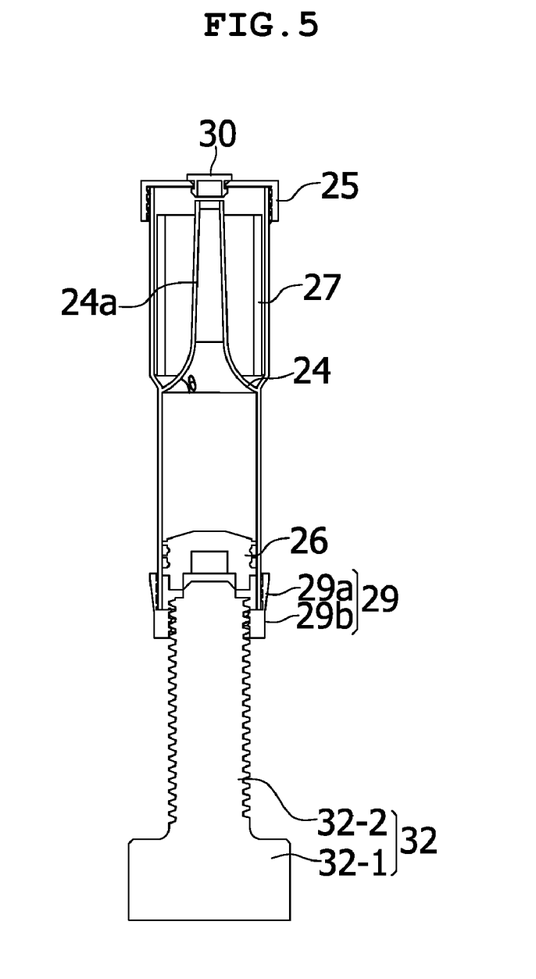
FIG. 5 is a front cross-sectional view of the blood separation container illustrated in FIG. 2.

FIG. 2 is an assembly perspective view of a blood separation container according to an embodiment of the present invention, FIG. 3 is an exploded perspective view of the blood separation container illustrated in FIG. 2, FIG. 4 is a cross-sectional perspective view of the blood separation container illustrated in FIG. 2, and FIG. 5 is a front cross-sectional view of the blood separation container illustrated in FIG. 2.

Referring to FIGS. 2 to 5, the blood separation container 20 according to the embodiment of the present invention includes a main body 21 defining an internal space divided into an upper fluid chamber 22 and a lower fluid chamber 23.

The main body 21 has a cylindrical structure and has an opened upper portion and an opened lower portion. The main body 21 may be made of a transparent material or a translucent material that allows a user to see the internal space.

The lower fluid chamber 23 of the main body 21 may have a diameter less than a diameter of the upper fluid chamber 22 such that a centrifugation is performed in a state in which the main body 21 is stably accommodated inside a centrifuge. Therefore, a stepped portion is formed at a boundary portion between the upper fluid chamber 22 and the lower fluid chamber 23.

When the main body 21 is accommodated in an accommodation unit of the centrifuge, the stepped portion formed at the boundary portion between the upper fluid chamber 22 and the lower fluid chamber 23 in the main body 21 may be locked to an entrance of the accommodation unit, and accordingly, a lower portion of the main body 21 may be spaced apart from a bottom surface of the accommodation unit in the centrifuge, thereby preventing the lower portion of the main body 21 from colliding with the bottom portion of the accommodation unit in the centrifuge and preventing the lower portion of the main body 21 from being damaged.

On the other hand, as illustrated in FIGS. 2 to 5, the main body 21 according to the present invention is formed to have a structure in which the upper fluid chamber 22 and the lower fluid chamber 23 have different diameters, but the structure is merely exemplary and the main body 21 according to the present invention is not limited to the structure illustrated in FIGS. 2 to 5. For example, the upper fluid chamber 22 and the lower fluid chamber 23 may be formed to have the same diameter.

In addition, the blood separation container 20 according to the embodiment of the present invention includes an upper cover 25 coupled to seal an upper opening of the main body 21, that is, the upper fluid chamber 12. To this end, in order to seal an opened portion of the upper fluid chamber 22, a thread 21a (see FIG. 3), which is coupled to a thread 25a (see FIG. 5) formed on an inner peripheral surface of the upper cover 25, is formed on an upper outer peripheral surface of the main body 21.

As illustrated in FIG. 3, an injection port 25b is provided at a central portion of the upper cover 25 so as to inject blood collected from a human body into a fluid passage 24a or extract a PRP, fibrin, a buffy coat, or the like separated inside the main body 21. It is preferable that the injection port 25b is sealed with a packing member 30 made of a soft material into which a needle of a syringe is inserted.

As illustrated in FIG. 3, in order to prevent the packing member 30 from being separated from the upper cover 25 at the time of opening the injection port 25b, it is preferable that the packing member 30 is disposed to be fixed to an upper portion of the upper cover 25 by a fixing pin 31. That is, since one side portion of the packing member 30 is disposed to be fixed to the upper cover 25 by the fixing pin 31 that passes through a fixing groove 30a defined in the one side portion of the packing member 30 and is inserted into a coupling groove 25c defined in the upper cover 25, a portion of the packing member 30 is fixed to the upper cover 25 to prevent the packing member 30 from being separated from the upper cover 25 even at the time of opening the injection port 25b, thereby reducing a risk of loss.

In addition, as illustrated in FIGS. 4 and 5, the blood separation container 20 according to the present invention includes a lower cover 26 that ascends along an inner peripheral surface of the lower fluid chamber 23 in a state in which an outer peripheral surface of the lower cover 26 comes into close contact with the inner peripheral surface of the lower fluid chamber 23 such that blood injected into the lower fluid chamber 23 does leak toward a lower opening of the main body 21.

The lower cover 26 is inserted through the lower opening of the main body 21 to seal the lower fluid chamber 23 and simultaneously, ascends toward a fluid collection part 24 inside the lower fluid chamber 23 in the state in which the outer peripheral surface of the lower cover 26 comes into close contact with the inner peripheral surface of the lower fluid chamber 23 when a strong pressure is applied upward.

In addition, as illustrated in FIGS. 2 and 5, the blood separation container 20 according to the present invention includes the fluid collection part 24 that is formed between the upper fluid chamber 22 and the lower fluid chamber 23 and includes the fluid passage 24a protruding upward from a central portion to communicate the upper fluid chamber 22 and the lower fluid chamber 23.

The fluid collection part 24 is formed to have a mountain-shaped structure protruding upward from an outer portion toward a central portion. The fluid passage 24a of the fluid collection part 24 may be disposed spaced a predetermined distance apart from an inner surface (ceiling surface) of the upper cover 25, a lower portion of the fluid collection part 24 communicates with the lower fluid chamber 23, and a top portion of the fluid collection part 24 communicates with the upper fluid chamber 22.

As illustrated in FIG. 5, the fluid passage 24a is formed such that an angle (θ) of an inlet side is in the range of 70° to 85°, preferably 80°, toward the lower fluid chamber 23. This is because a collect rate of the buffy coat is increased by minimizing a loss of a portion of the buffy coat due to the adhering of the buffy coat to an inner surface of the fluid passage 24a during extracting of the buffy coat through the fluid passage 24a. Actually, when the angle of the inlet side in the fluid passage 24a was less than 70°, the collect rate of the buffy coat was significantly decreased.

As illustrated in FIG. 3, the blood separation container 20 according to the present invention may include a coagulation catalyst body 27 that has a cylindrical structure and is inserted into the upper fluid chamber 22 to function as a catalyst such that a PRP and a PPP rapidly coagulate at the time of coagulating the PRP and the PPP by using the centrifuge.

The coagulation catalyst body 27 may be made of a glass material and may be disposed such that an outer peripheral surface of the coagulation catalyst body 27 comes into contact with or is spaced a predetermined distance apart from the inner peripheral surface of the upper fluid chamber 22. Preferably, in order to prevent the coagulation catalyst body 27 from being damaged due to independent rotation inside the upper fluid chamber 22 during the centrifugation using the centrifuge, the coagulation catalyst body 27 is disposed such that the outer peripheral surface of the catalyst body 27 comes into contact with the inner peripheral surface of the upper fluid chamber 22.

On the other hand, although not illustrated, the coagulation catalyst body 27 according to the present invention may be disposed in the lower fluid chamber 23 instead of the upper fluid chamber 22.

As illustrated in FIG. 3, the blood separation container 20 according to the present invention may further include a reinforcement member 28 (see FIG. 3) coupled to a lower surface of the lower cover 26 so as to support the lower cover 26 from an external force applied to a lower portion of the lower cover 26 by an ascending member 32.

In addition, the blood separation container 20 according to the present invention includes a release prevention member 29 screwed to a lower portion of the main body 21 so as to prevent the lower cover 26 from being released from the main body 21 due to a strong rotational force during the centrifugation using the centrifuge.

As illustrated in FIGS. 2 to 4, the release prevention member 29 includes a first coupling portion 29a and a second coupling portion 29b that communicates with the first coupling portion 29a so as to be coupled, in a bolt structure, to the ascending member 32, on an outer peripheral surface of which a thread 32-2a is formed, a thread 29a-1 being formed on an inner peripheral surface of the first coupling portion 29a so as to be coupled to a thread 21b formed on the outer peripheral surface of the main body 21, and a thread 29b-1 being formed on an inner peripheral surface of the second coupling portion 29b. At this time, the second coupling portion 29b is formed to have a diameter less than a diameter of the first coupling portion 29a so as not to come into contact with the first coupling portion 29a when the ascending member 32 is screwed to penetrate the second coupling portion 29b.

As illustrated in FIGS. 3 and 4, the ascending member has a bolt structure. Specifically, the ascending member 32 includes an operation unit 32-1 that is operable with a user hand and a coupling unit 32-2 that has one side portion integrally coupled to the operation unit 32-1 and the other side portion inserted into the second coupling portion 29b of the release prevention member 29 and is coupled to the second coupling portion 29b of the release prevention member 29 through a male thread formed on an outer peripheral surface of the coupling unit 32-2.

The thread 32-2a is formed on an outer peripheral surface of a region of the ascending member 32 such that a portion of the coupling unit 32-2 is coupled to the thread 29b-1 formed on the inner peripheral surface of the second coupling portion 29b (see FIG. 3) in the release prevention member 29, the region of the ascending member 32 being inserted into the second coupling portion 29b. Therefore, the ascending member 32 is inserted into and screwed to the second coupling portion 29b of the release prevention member 29, is coupled to the second coupling portion 29b so as to be elevatable, and ascends the lower cover 26 disposed in the lower fluid chamber 23 through an ascending operation to vary a variation in a volume of the lower fluid chamber 23.

Figure 6:
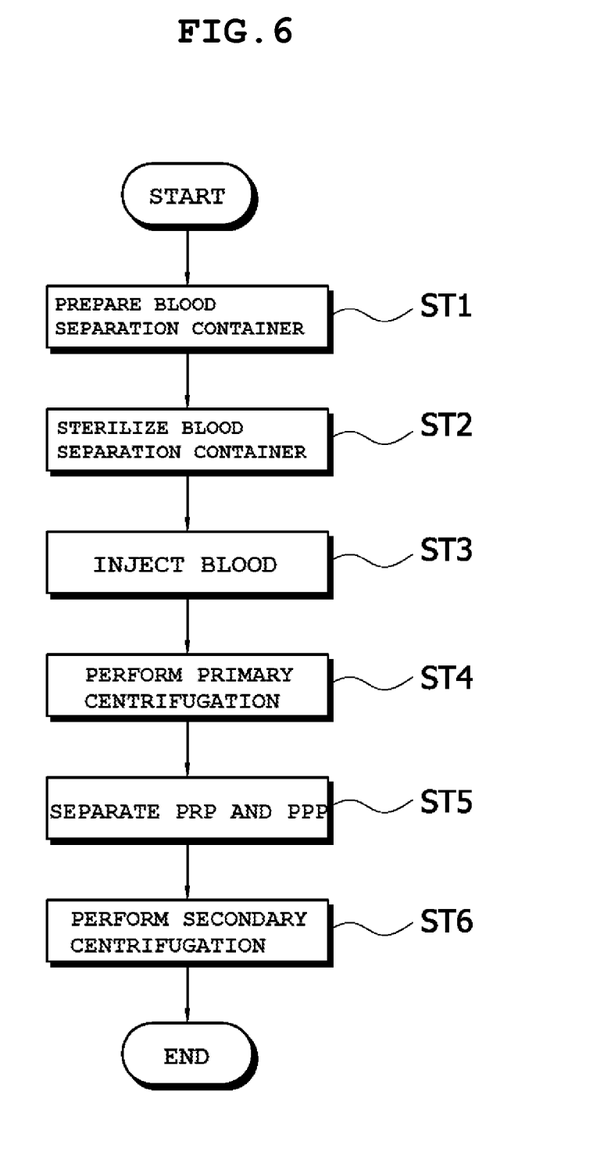
FIG. 6 is a flowchart of a PRP and PPP separating and coagulating method according to an embodiment of the present invention.

FIG. 6 is a flowchart of a PRP and PPP separating and coagulating method according to an embodiment of the present invention.

First, referring to FIGS. 2 to 6, a blood separation container 20 is prepared (ST1).

The preparing of the blood separation container 20 is performed by coupling an upper cover 25 to an upper portion of a main body 21 to seal an upper portion of the upper fluid chamber 22 in a state in which a coagulation catalyst body 27 is inserted into an upper inside of the main body 21, that is, the upper fluid chamber 22 (or a lower fluid chamber 23), and inserting a lower cover 26 to a lower inside of the main body 21, that is, the lower fluid chamber 23 by press fit to seal a lower portion of the lower fluid chamber 23. A release prevention member 29 may be coupled to an outer surface of the main body 21.

Next, a sterilization treatment is performed on the blood separation container 20 in the state in which the coagulation catalyst body 27 is inserted into the upper fluid chamber 22 (ST2).

Next, blood collected from a human body through an injection port 25b of an upper cover 25 is injected into the main body 21, that is, the lower fluid chamber 23 through a fluid passage 24a of a fluid collection part 24 (ST3).

Next, after the blood separation container 20, in which the blood is injected into the lower fluid chamber 23, is accommodated in a centrifuge, a primary centrifugation is performed on the blood to separate a red blood cell, a PRP, and a PPP inside the lower fluid chamber 23 (ST4).

Next, the blood separation container 20, in which the primary centrifugation is completed, is carried out from the centrifuge, and then, an ascending member 32 is inserted into the lower fluid chamber 23 through a second coupling portion 29b of a release prevention member 29. Next, among the blood cell, the PRP, and the PPP inside the lower fluid chamber 23, the PRP and the PPP except for the red blood cell are introduced into the upper fluid chamber 22 through the fluid passage 24a of the fluid collection part 24 to separate the PRP and the PPP from the red blood cell by rotating the ascending member 32 in a clockwise direction to ascend the lower cover 26 along an inner peripheral surface of the lower fluid chamber 23 (ST5).

After that, in a state in which the PRP and the PPP are introduced into the upper fluid chamber 22 and are separated from the red blood cell, after the ascending member 32 is separated from the release prevention member 29, the blood separation container 20 is accommodated in the centrifuge to perform a secondary centrifugation (ST6). The processes are performed for 3 minutes to 5 minutes to coagulate the PRP and the PPP introduced into the upper fluid chamber 22 to thereby extract fibrin (or a buffy coat).

Since the secondary centrifugation performed in step ST6 is performed in the state in which the coagulation catalyst body 27 made of a glass material is inserted into the upper fluid chamber 22, a coagulation time of the PRP and the PPP is reduced, as compared with a case where the secondary centrifugation is performed in the absence of the coagulation catalyst body 27.

In order to confirm the coagulation rate of the PRP and the PPP through the secondary centrifugation, the secondary centrifugation was performed in the state in which the coagulation catalyst body 27 was inserted into the upper fluid chamber 22, and as a result, about 3 minutes to about 5 minutes were taken until the PRP and PPP coagulated. On the contrary, when the secondary coagulation was performed in a state in which the coagulation catalyst body according to the present invention was not inserted into the upper fluid chamber 22, more time was taken until the PRP and PPP are coagulated.

As described above, according to the present invention, since the secondary coagulation is performed in the state in which the coagulation catalyst body 27 is inserted into the upper fluid chamber 22, the coagulation time of the PRP and PPP may be significantly reduced, thereby improving extraction productivity of the fibrin (or the buffy coat).

While the present invention has been shown and described in connection with the exemplary embodiments, it will be apparent to those skilled in the art that modifications and variations can be made without departing from the spirit and scope of the invention as defined by the appended claims.

The invention claimed is:

1. A blood separation container comprising:
a main body defining an inner space divided into an upper fluid chamber and a lower fluid chamber;
an upper cover sealing the upper fluid chamber;
a lower cover ascending along an inner peripheral surface of the lower fluid chamber in such a state that an outer peripheral surface of the lower cover comes into close contact with the inner peripheral surface of the lower fluid chamber;
a fluid collection part which is formed between the upper fluid chamber and the lower fluid chamber and includes a fluid passage protruding upward from a central portion to communicate the upper fluid chamber and the lower fluid chamber;
a release prevention member which is coupled to an outer peripheral surface of the main body and includes a first coupling portion and a second coupling portion that communicates with the first coupling portion, a thread being formed on an inner peripheral surface of the first coupling portion so as to be coupled to a thread formed on a lower outer peripheral surface of the main body, and a thread being formed on an inner peripheral surface of the second coupling portion so as to have a diameter less than a diameter of the first coupling portion; and
an ascending member which is inserted into and coupled to the second coupling portion of the release prevention member, a portion of which is screwed to the second coupling portion of the release prevention member in a bolt structure, and which is carried in the lower fluid chamber of the main body and varies in a variation in a volume of the lower fluid chamber by ascending the lower cover coming into close contact with the inner peripheral surface of the lower fluid chamber.

2. A blood separation container comprising:
a body defining an inner space divided into an upper fluid chamber and a lower fluid chamber;
an upper cover sealing the upper fluid chamber:
a lower cover ascending along an inner peripheral surface of the lower fluid chamber in such a state that an outer peripheral surface of the lower cover comes into close contact with the inner peripheral surface of the lower fluid chamber; and
a fluid collection part which is formed in a funnel shape and includes a fluid passage communicating the lower fluid chamber and the upper fluid chamber, the funnel shape having a mountain-shaped structure that extends from an inner sidewall of the main body to a central portion of the main body at a boundary between the upper fluid chamber and the lower fluid chamber and protrudes toward the upper fluid chamber from the inner sidewall to the central portion,
wherein the fluid passage is formed such that an angle of an inlet side in the fluid passage, which is opposed to the lower fluid chamber, is in the range of 70° to 85°.

3. The blood separation container of claim 2, further comprising a release prevention member coupled to a lower outer peripheral surface of the main body,
wherein the release prevention member includes a first coupling portion and a second coupling portion that communicates with the first coupling portion, a thread being formed on an inner peripheral surface of the first coupling portion so as to be coupled to a thread formed on a lower outer peripheral surface of the main body, and a thread being formed on an inner peripheral surface of the second coupling portion so as to have a diameter less than a diameter of the first coupling portion.

4. The blood separation container of claim 3, further comprising an ascending member inserted into and coupled to the second coupling portion,
- wherein a portion of the ascending member is screwed to the second coupling portion of the release prevention member in a bolt structure, and the ascending member is carried in the lower fluid chamber of the main body and varies in a variation in a volume of the lower fluid chamber by ascending the lower cover coming into close contact with the inner peripheral surface of the lower fluid chamber.

5. A blood separation container comprising:
- a body defining an inner space divided into an upper fluid chamber and a lower fluid chamber;
- an upper cover sealing the upper fluid chamber;
- a lower cover ascending along an inner peripheral surface of the lower fluid chamber in such a state that an outer peripheral surface of the lower cover comes into close contact with the inner peripheral surface of the lower fluid chamber;
- a fluid collection part which is formed between the upper fluid chamber and the lower fluid chamber and includes a fluid passage protruding upward from a central portion to communicate the upper fluid chamber and the lower fluid chamber; and
- a coagulation catalyst body made of a circular tube including a glass material and inserted into the upper fluid chamber or the lower fluid chamber to function as a catalyst such that a platelet rich plasma (PRP) and a platelet poor plasma (PPP) rapidly coagulate at the time of coagulating the PRP and the PPP by using a centrifuge.

6. The blood separation container of claim 5, further comprises a release prevention member coupled to a lower outer peripheral surface of the main body,
- wherein the release prevention member includes a first coupling portion and a second coupling portion that communicates with the first coupling portion, a thread being formed on an inner peripheral surface of the first coupling portion so as to be coupled to a thread formed on a lower outer peripheral surface of the main body, and a thread being formed on an inner peripheral surface of the second coupling portion so as to have a diameter less than a diameter of the first coupling portion.

7. The blood separation container of claim 6, further comprising an ascending member inserted into and coupled to the second coupling portion,
- wherein a portion of the ascending member is screwed to the second coupling portion of the release prevention member in a bolt structure, and the ascending member is carried in the lower fluid chamber of the main body and varies in a variation in a volume of the lower fluid chamber by ascending the lower cover coming into close contact with the inner peripheral surface of the lower fluid chamber.

* * * * *